United States Patent [19]

Peak

[11] 4,062,228

[45] *Dec. 13, 1977

[54] POWDER MOISTURE METER

[75] Inventor: William H. Peak, Albany, N.Y.

[73] Assignee: Donald P. Matula, Schenectady, N.Y.; a part interest

[21] Appl. No.: 460,569

[*] Notice: The portion of the term of this patent subsequent to Oct. 13, 1993

[22] Filed: Apr. 12, 1974

[51] Int. Cl.² .............................................. G01N 5/00
[52] U.S. Cl. ..................................... 73/74; 73/32 R; 73/427
[58] Field of Search ..................... 73/73, 74, 76, 427, 73/32 R

[56] References Cited

U.S. PATENT DOCUMENTS

| 641,052 | 1/1900 | Strauss | 73/427 |
| 690,530 | 1/1902 | Smith | 73/427 X |
| 2,280,617 | 4/1942 | Bell | 73/74 |
| 2,647,394 | 8/1953 | Schaeperklaus | 73/73 X |

FOREIGN PATENT DOCUMENTS

| 913,355 | 9/1946 | France | 73/73 |

Primary Examiner—James J. Gill
Attorney, Agent, or Firm—Gerhard K. Adam

[57] ABSTRACT

A powder moisture meter, comprising an open-mouthed container comprising first and second transparent wall portions, said second wall portion being disposed between said first wall portion and the container mouth, first graduated scale means at said first wall portion for calibrating said meter, second graduated scale means at said second wall portion for directly determining the moisture content of said powder.

6 Claims, 1 Drawing Figure

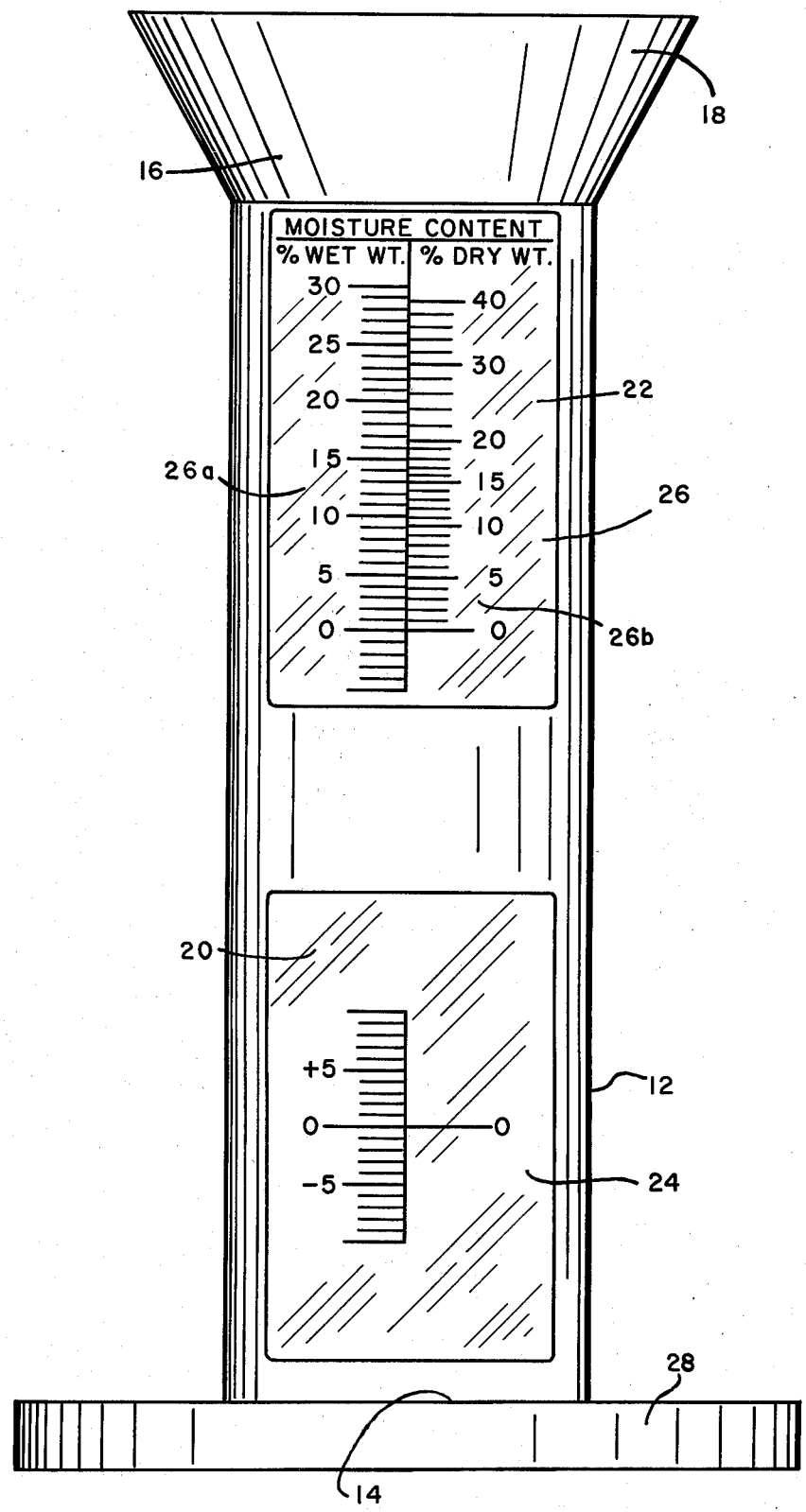

POWDER MOISTURE METER

BACKGROUND OF THE INVENTION

The present invention relates to a moisture meter, particularly to one of a direct-reading type.

Prior art devices for measuring soil moisture content suffer from a number of drawbacks. In particular, such devices that have a movable scale are not completely satisfactory because the scale can be moved inadvertently or can become loose to the point where they might lead to inaccurate moisture content readings.

The present invention overcomes such drawbacks by providing a moisture meter having no movable parts in the operation thereof and providing a direct moisture content reading without any need to resort to weighing the moisture measuring apparatus.

BRIEF DESCRIPTION OF THE DRAWING

FIG. 1 is a front elevation view of the moisture meter of the present invention.

PREFERRED EMBODIMENT

Referring to FIG. 1, moisture meter 10, which can be used to determine the moisture content of a powder (defined herein to include, without limitation, soils), comprises a container portion 12 preferably having a cylindrical configuration (a rectangular or other cross-sectional configuration also being satisfactory) and one end 14 closed, with the opposite end 16 open to form a mouth leading into the interior of the container portion. The meter 10 preferably includes a funnel-shaped portion 18 located at the mouth end 16, the funnel portion 18 flaring outwardly in the direction away from the container portion 12. The container portion 12 comprises a first wall portion 20 and a second wall portion 22, both of which are transparent (defined herein to include translucent), a first and second graduated scales 24 and 26 being respectively located at the first and second transparent wall portions 20 and 22.

The first scale 24 is used for calibrating the meter 10 and the second scale 26 is used for directly reading the moisture content of the powder sample, as described below. The first scale 24 is located below the second scale 26, the latter being between the first scale 24 and the mouth. It is preferred that the second scale 26 comprise two component scales 26a and 26b, one of these (e.g., 26a) being linearly graduated and providing directly a moisture (percentage) content reading on the basis of the wet weight of the specimen and the other 26(b) being non-linearly (e.g., geometrically) graduated and providing directly a moisture (percentage) content reading on the basis of the dry weight of the specimen. It is preferred that the wall portion of the container portion 12 aside from the parts at which the scales are located, be substantially opaque to facilitate reading the level of fluids contained therein. It is further preferred that the meter 10 include a base portion 28, although this is not an indispensable feature of the present invention. According to a preferred embodiment, the first (calibrating) scale 24 be graduated and extend from minus 10 to plus 10, for example. The scale divisions of scales 24 and 26a can be substantially equal.

In the use of the moisture meter 10, the preferred first step is to calibrate the meter, this being done to permit adjustment for the variation in the characteristics of the various powders to be tested, i.e., the specific gravity (where soil moisture absorption rate is to be measured, for variation in the moisture absorption rate and/or the moisture absorption capacity) of the various powders that are to be measured for moisture content. Such calibration involves obtaining a sample of moist powder to be measured, e.g., about a 1000 gram sample, obtaining a predetermined quantity (e.g., about 300 grams) of this moist powder, and drying (preferably stove or oven drying) the quantity to a constant weight level. As further steps in the calibration, the container portion 12 is filled with a liquid (preferably, water) to the initial water level setting (e.g., the zero point) of the first (calibrating) scale 24, a second quantity (e.g., 600 grams) of the powder is placed in the container portion 12 with sufficient agitation thereof to completely suspend the sample powder in the fluid, and then the level of the liquid-powder suspension is read on the graduated (direct reading) second scale 26, that is, on the component scale 26a that gives a moisture content reading on the basis of the wet weight of the sample of soil. Having done this the weight loss of the first quantity of powder, attributable to the moisture loss brought about by the drying step, is determined and from this the moisture content on the basis of the wet weight of the soil sample is calculated. The moisture content (on the basis of wet weight of the soil sample) of the undried second quantity is determined directly as the reading from the scale component 26a of the second scale 26, this undried sample moisture content being compared with the calculated moisture content for the dried sample. If there is any difference in moisture content between the dried and undried quantities, this differential is provided for in the subsequent moisture measurements for other samples of powder of comparable specific gravity.

Where the dried powder moisture content exceeds that of the undried powder, this differential is compensated for by filling the liquid in the subsequent moisture measurement operation to a level equal to initial water level setting (i.e., the zero level of the calibration scale) plus this differential, e.g., if the moisture content (calculated) for the dried sample is 8.0% and that for the undried (i.e., the direct moisture measurement) is 7.5%, the water level for subsequent measurements is initially brought to +0.5%. Where the direct moisture reading for the undried powder exceeds that for the dried powder, e.g., if the differential is 1%, the liquid level initially is set at the level equal to the initial water setting less this differential value.

To make a moisture measurement on an as-received powder (e.g., soil) sample, the water level in the container 12 is brought to the initial water level setting plus or minus the differential determined in the calibration step. Where there is no difference determined in the calibration step between the dried and undried (as received) powder, the fluid level is set at the initial water level setting (i.e., at the zero point of the calibration scale). The lower part of the container portion 12 disposed below the lower scale 24 has a volume at least sufficient to hold a quantity of liquid that is sufficient for substantially completely suspending the powder sample therein.

Thereafter, a pre-determined quantity (e.g., 600 grams) of the as-received powder is introduced into the liquid and agitated sufficient to achieve substantially complete suspension therein, after which the level of this suspension is determined with respect to the moisture scale 26, from which scale 26 the moisture reading is directly obtained, the reading from scale 26a being on the basis of the wet weight of the soil sample and from 26b being on the dry weight of the sample.

This process can be repeated for other samples of the same powder. Where other powders (soils) are to be tested for moisture content, it is suggested that the moisture meter 10 be re-calibrated in the manner described above.

It is preferred that the volume of the container interior space located between the zero point of the calibration scale 24 and the zero point of the moisture scale 26 be substantially equal to the general volume of the sample quantity for the type of powder whose moisture is to be measured.

I claim:

1. A powder moisture meter, comprising:
   a. an open-mouthed container comprising first and second transparent wall portions, said second wall portion being disposed between said first wall portion and the container mouth;
   b. first graduated scale means at said first wall portion for calibrating said meter by adjusting according to the particular characteristics of said powder to be tested, the direct determination of the moisture content of said powder;
   c. second graduated scale means at said second wall portion for directly determining the moisture content of said powder, said second scale means comprising divisions for measuring said moisture content on at least one of a wet weight and dry weight bases, said first scale means permitting the reading of said second scale means to be so adjusted.

2. A moisture meter as in claim 1, wherein said container comprises substantially opaque further wall portions at substantially the balance of the wall thereof.

3. A moisture meter as in claim 1, wherein said container comprises a funnel shaped portion at said mouth.

4. A moisture meter as defined in claim 1, wherein said second scale comprises at least two component scales, a first component scale being linear and a second component scale being non-linear, said linear first component scale providing a moisture content reading on the basis of the wet weight of said powder sample and said second component scale providing said reading on the basis of the dry weight of said powder sample.

5. A moisture meter as defined in claim 1, wherein said first and second scales are separated by an internal volume of said container substantially equal to the volume of a sample of said powder in a substantially dry condition.

6. A moisture meter as defined in claim 1, wherein said container defines a volume disposed between said first scale means and the closed end of said container, said volume being at least equal to the amount of liquid required to suspend said powder.

* * * * *